United States Patent [19]

Goh et al.

[11] Patent Number: 4,654,074
[45] Date of Patent: Mar. 31, 1987

[54] 2-CHLORO-N-(4,6-DIMETHOXY-5-PYRIMIDINYL)-N-[1,(1-PYRAZOLYL)ETHYL]ACETAMIDE, HERBICIDAL COMPOSITION COMPRISING SAID COMPOUND, AND METHOD OF CONTROLLING WEEDS USING SAID COMPOUND

[75] Inventors: Atsushi Goh, Ushiku; Mami Nakamura, Ami; Keiji Endo, Ami; Mitsuru Hikido, Ami, all of Japan

[73] Assignee: Mitsubishi Petrochemical Co., Ltd., Tokyo, Japan

[21] Appl. No.: 829,995

[22] Filed: Feb. 18, 1986

[30] Foreign Application Priority Data

Feb. 19, 1985 [JP] Japan .................................. 60-31370

[51] Int. Cl.⁴ .................... A01N 43/56; C07D 247/02
[52] U.S. Cl. ......................................... 71/92; 544/319
[58] Field of Search ................... 544/322, 319; 71/88, 71/92

[56] References Cited

U.S. PATENT DOCUMENTS 4,243,408  1/1981  Chan ........................................ 71/92
4,369,056  1/1983  Thomas et al. ......................... 71/92
4,494,983  1/1985  Eicken et al. ........................... 71/92

FOREIGN PATENT DOCUMENTS 2127404  4/1984  United Kingdom ................ 544/322

Primary Examiner—Glennon H. Hollrah
Assistant Examiner—R. Lelkes
Attorney, Agent, or Firm—Wenderoth, Lind & Ponack

[57] ABSTRACT

2-Chloro-N-(4,6-dimethoxy-5-pyrimidinyl)-N-[1-(1-pyrazolyl)ethyl]acetamide of the following formula:

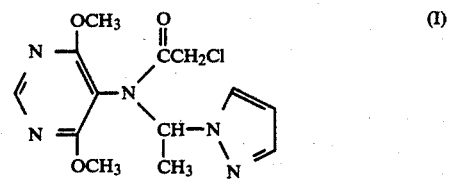

a herbicidal composition comprising a herbicidally effective amount of the compound of formula (I); and a method of controlling weeds which comprises applying a herbicidally effective amount of the formula (I) to the locus where the weeds are growing or will grow.

8 Claims, No Drawings

2-CHLORO-N-(4,6-DIMETHOXY-5-PYRIMIDINYL)-N-[1,(1-PYRAZOLYL)ETHYL-]ACETAMIDE, HERBICIDAL COMPOSITION COMPRISING SAID COMPOUND, AND METHOD OF CONTROLLING WEEDS USING SAID COMPOUND

This invention relates to a novel compound useful for controlling weeds, a herbicidal composition comprising it as an active ingredient, and a method of controlling weeds using the compound. Particularly, this invention relates to a novel compound useful for selectively controlling or combatting weeds without causing undesirable phytotoxicity to crops, a selective herbicidal composition comprising it as an active ingredient, and a method of selectively controlling weeds using the aforesaid compound.

More specifically, this invention relates to 2-chloro-N-(4,6-dimethoxy-5-pyrimidinyl)-N-[1-(1-pyrazolyl)ethyl]acetamide of the following formula (I):

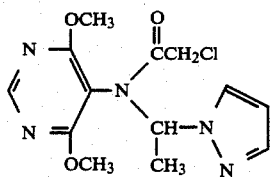

This invention also pertains to a herbicidal composition comprising the compound of formula (I) as an active ingredient and a herbicidally acceptable diluent or carrier, and to a method of controlling weeds using the compound of formula (I).

UK Patent Application GB No. 2127404 (published on Apr. 11, 1984; corresponding to Japanese Laid-Open Patent Publication No. 1167/1985) discloses pyrimidine compounds substituted in the 5-position by a chloroacetylamino group which are represented by formula I given below and can encompass very many compounds, their use as herbicides, agricultural compositions for such use and the preparation of the above compounds.

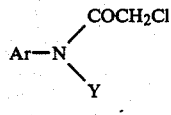

In formula I, Ar represents substituted or unsubstituted 5-pyrimidinyl, and Y represents many groups including groups represented by $R_2A_z$ in which $R_2$ is $CH_2$ or $CH_2-CH_2$ unsubstituted or substituted by $C_1-C_5$ alkyl, and $A_z$ represent many groups including a di- or triazole linked by one of its nitrogen atoms to $R_2$.

As a preferred sub-group of the compounds of formula I which can encompass very many compounds, page 3 of GB No. 2127404A describes compounds represented by the following formula Ia.

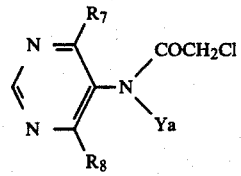

wherein $R_7$ and $R_8$, independently, are $C_{1-4}$alkyl, $C_{1-4}$alkoxy, $C_{1-4}$alkylthio or di($C_{1-4}$alkyl) amino, and Ya is $C_{3-5}$alkenyl or $C_{3-5}$alkinyl unsubstituted or monosubstituted by halogen selected from F, Cl, Br or is $C_{1-3}$alkoxy-$C_{1-3}$alkyl unsubstituted or mono-substituted by $C_{1-4}$alkoxy; or is $C_{3-5}$alkinoxy-$C_{1-3}$alkyl; or is $C_{3-5}$alkenoxy-$C_{1-3}$alkyl; or is $CH_2-CH=C=CH_2$; or is $CH_2A'_z$, $CHR_5-CHR_5'=NO(C_{1-4}$alkyl), $CH(R_6)B'$ or $CH(R_6)COY'_1$, wherein $A'_z$ is a heteroring selected from 1-diazolyl, 1-triazolyl, a 5 membered aromatic heteroring linked by a C-atom of said ring to the $CH_2$ group and having 1 to 3 heteroatoms selected from the group consisting of O, S or N, and 2-pyrimidinyl whereby the heteroring may be unsubstituted or substituted by 1 or 2 groups selected from $C_{1-4}$alkyl, halogen (e.g. Cl), $C_{1-4}$alkoxy (e.g. $OCH_3$), $C_{1-4}$alkylthio (e.g. $SCH_3$), and di($C_{1-4}$alkylamino), (e.g. $N(CH_3)_2$), B' is $N(CH_3)COCH_3$; 2-oxo-3-benzthiazolidinyl unsubstituted or mono-substituted by halogen selected from F, Cl and Br, $Y'_1$ is di-($C_{1-4}$alkyl)amino or $C_{1-4}$alkoxy, and $R_5$, $R'_5$ and $R_6$ are as defined above.

In a preferred sub-group of compounds of formula 1a, one of $R_7$ and $R_8$ is selected from the group consisting of $C_{1-4}$alkoxy and di($C_{1-4}$alkyl)amino. Particularly suitable $C_{1-4}$alkoxy significances of $R_7$ and $R_8$ are e.g. $CH_3O$, $C_2H_5O$, i-$C_3H_7O$ and n-$C_4H_9O$, especially i-$C_3H_7O$.

A particularly suitable di($C_{1-4}$alkyl)amino significance of $R_7$ and $R_8$ is i.a. $N(CH_3)_2$. Where any of $R_7$ and $R_8$ is $C_{1-4}$alkyl or $C_{1-4}$alkylthio it is preferably $CH_3$ or $CH_3S$ resp.

Examples of very suitable $A'_z$ significances are 1,2,4-triazol-1-yl, 2-methyl-1,3,4-oxadiazol-5-yl, 3-methyl-1,2,4-oxadiazol-5-yl, 3-methyl-isoxazol-5-yl, 2-methyl-thiazol-4-yl, 2-thienyl, 2-pyrimidinyl and 1-pyrazolyl, particularly the latter.

Thus, GB No. 2127404A describes the compounds of formula I which would include the compound of formula (I) in accordance with this invention if one chooses a 4,6-dimethoxy-5-pyrimidinyl group as Ar, $R_2-A_z$ as Y, $CH_2$ substituted by methyl as $R_2$ and pyrazole linked by one of its nitrogen atoms to $R_2$ as $A_z$. However, this patent document does not at all suggest the selection of such a combination of parameters, and formula Ia specifically given as a preferred sub-group of the compounds of formula I which can encompass very many compounds does not include the compound of formula (I) in accordance with this invention.

Furthermore, the compound of formula (I) provided by this invention is not at all included in the many examples of the compounds I specifically given in GB No. 2127404 A. Among the compounds illustrated in GB No. 2127404A, compound 35 of the following formula which falls within formula Ia is most analogous to the compound (I) of the present invention.

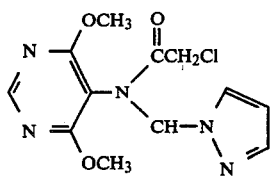

Compound 35

The above UK specification states that the compounds are relatively less toxic towards crops, e.g. against grassy crops such as a small grain (winter cereals, rice) or corn and particularly against broad leaved crops such as cotton, sugar beet, potato, sunflower rape or flax, than towards weeds, and that the compounds are therefore also indicated for use as selective herbicides in a crop locus. It is only with regard to compound 35 that the UK specification shows specific data on herbicidal effects. In these data, metolachlor [2-chloro-N(2-ethyl-6-methylphenyl)-N-(2-methoxy-1-methylethyl)acet amide] represented by the following formula is used as a standard.

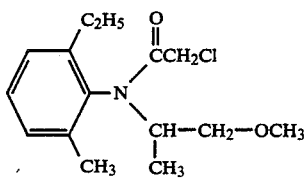

Investigations of the present inventors have shown that compound 35 of GB No. 2127404A show superior activity against weeds of the genus Panicum, purple nutsedge (*Cyperus rotundus* L.) which is normally difficult to control, and some broad-leaved weeds to "alachlor" [2-chloro-2',6'-diethyl-N-(methoxymethyl)acetanilide] conventionally used worldwide as a herbicide in this field (as a soil treating agent against gramineous weeds) in soybean and corn fields, but has the same defect as "alachlor" with regard to its selectivity for crops. Specifically, compound 35 has the defect of causing phytotoxicity to broad-leaved crops, particularly sugar beet and cotton.

The present inventors have found as a result of field tests under natural conditions that when the above known compound 35 was applied at rates which showed a satisfactory herbicidal effect against weeds growing in the fields, it caused negligible phytotoxicity to crops.

The present inventors have undertaken research to develop herbicidally active compounds which are free from the trouble of causing phytotoxicity. Consequently, they have succeeded in synthesizing a compound of the following formula (I)

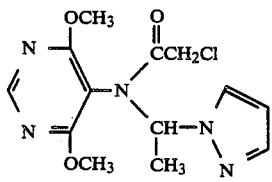

which can be included within general formula I given in GB No. 2127404A but is not encompassed within general formula Ia recommended as a preferred sub-group in the above UK specification nor specifically disclosed in the UK specification and which is not described in the prior known literature. It has further been found that the compound of formula (I) exhibits an excellent herbicidal effect against weeds growing in upland farms in treatment at the stage of emergence or at a stage near it and at the growing stage, particularly in pre-emergence treatment.

Investigations of the present inventors have also shown that the compound of formula (I) shows an excellent control effect against weeds, particularly gramineous weeds, with low phytotoxicity to crops, particularly without substantial phytotoxicity to soybean, sugar beet and cotton, and therefore that the compound (I) exhibits an excellent selective control effect against weeds in the locus where such a crop is cultivated or will be cultivated.

The present inventors have also found that the compound of formula (I) in accordance with this invention is much less toxic to crops than the known compound 35, and exhibits a herbicidal effect equivalent to, or higher than, the compound 35 in fields under natural conditions.

The present inventors have further found that other analogous compounds that can be encompassed by general formula I in GB No. 2127404A, for example compounds which are analogous to the compound (I) of the invention and have the

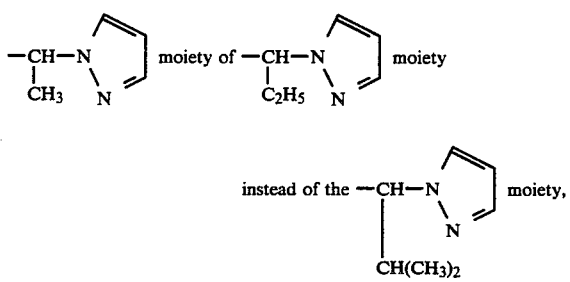

do not show a practical herbicidal effect, and only the compound of formula (I) provided by this invention exhibits the aforesaid excellent selective herbicidal effect.

It is an object of this invention therefore to provide 2-chloro-N-(4,6-dimethoxy-5-pyrimidinyl)-N-[1-(1-pyrazolyl)ethyl] acetamide of formula (I).

Another object of this invention is to provide a herbicidal composition comprising the compound of formula (I) as an active ingredient.

Still another object of this invention is to provide a method of controlling weeds using the compound of formula (I).

The above and other objects of this invention along with its advantages will become apparent from the following description.

The novel compound of this invention can be produced, for example, by the following route.

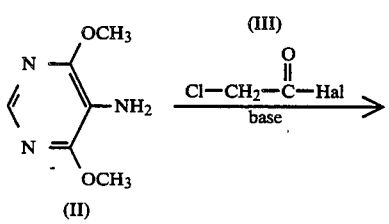

-continued

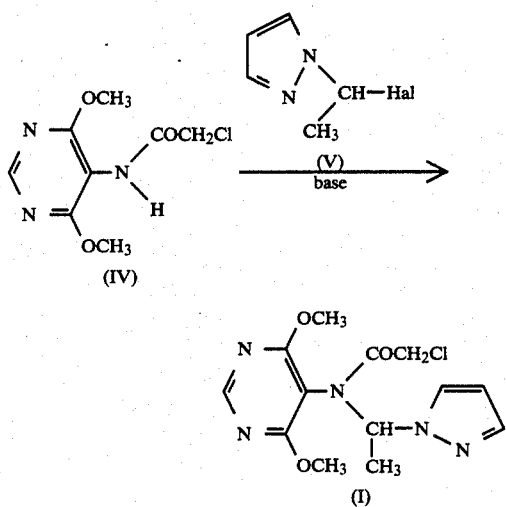

In the above formulae, Hal represents a halogen atom.

The first step of the above reaction route is the acylation of the amine, and can be carried out easily under the same conditions as in the acylation of general amines. This reaction can be carried out by using 1 equivalent of the compound (II) and, for example, 1 to 2, preferably 1 to 1.2 equivalents, of the compound in an organic solvent. Examples of the organic solvent are aromatic hydrocarbons such as toluene and xylene, ethers such as diethyl ether, tetrahydrofuran and dioxane, halogenated hydrocarbons such as chloroform and carbon tetrachloride, ethyl acetate, acetonitrile, and dimethylformamide and dimethyl sulfoxide. By using a base such as pyridine, triethylamine, sodium hydroxide, potassium hydroxide, sodium carbonate and potassium carbonate as a dehydrohalogenation agent, the compound (IV) can be obtained in higher yields. There is no particular restriction on the reaction temperature. For example, the reaction can be carried out under ice cooling or at temperatures up to the refluxing temperature of the solvent. Preferably, it is carried out under ice cooling or at temperatures up to about 40° C. The reaction time varies depending upon the reaction temperature and the type of the reagent used. For example, it is about 1 to about 20 hours. After the reaction, the compound (IV) can be isolated by treating the reaction mixture in accordance with a conventional method such as recrystallization.

The second step is the N-alkylation of the amide which can be carried out under ordinary alkylating conditions. The reaction can be carried out in an organic solvent or a two-layer system of water and an organic solvent in the presence of a phase transfer catalyst. By using a dehydrohalogenation agent, the reaction can give the compound (I) in high yields. Examples of the solvent and the dehydrohalogenation agent are the same as those given above with regard to the acylation reaction in the first step. Sodium hydride and sodium ethoxide may also be used as the dehydrohalogenation agent. The reaction can be carried out by using 1 equivalent of the compound (IV) and, for example, 1 to 2 equivalents, preferably 1 to 1.2 equivalents, of the compound (V). When the reaction is carried out in the two-layer system, it is possible to use 1 to 50% by weight, preferably 5 to 30% by weight, based on the compound (IV), of a phase transfer catalyst, for example a tetraammonium salt such as tetramethyl ammonium bromide, tetrabutyl ammonium bromide and benzyl tributyl ammonium bromide, and a quaternary phosphonium salt such as tetraphenyl phosphonium bromide. There is no particular restriction on the reaction temperature, and for example, the reaction can be carried out under ice cooling or at temperatures up to the refluxing temperature of the solvent, preferably at room temperature to about 100° C. The rection time varies depending upon the reaction temperature and the type of the reagent used. For example, reaction periods of about 1 to about 20 hours may be employed. After the reaction, the compound (I) of the invention can be isolated by treating the reaction mixture in accordance with a conventional method such as recrystallizaion or column chromatography.

The compound of this invention has herbicidal activity on weeds, and exhibits its effect at the stage of emergence or at a stage near it or at the active growth stage of the weeds. It exhibits the strongest herbicidal effect in the pre-emergence treatment of weeds.

According to this invention, therefore, there can be provided a method of controlling weeds which comprises applying a herbicidally effective amount of the compound of formula (I) to the locus where weeds are growing or will be grown.

The invention also provides a herbicidal composition comprising a herbicidally effective amount of the compound of formula (I) as an active ingredient and a herbicidally acceptable diluent or carrier.

The compound of formula (I) of this invention is effective against gramineous weeds such as barnyard grass (*Echinochloa crus-galli*), fingergrass (*Digitaria sanguinalis*), green foxtail (*Setaria viridis*), Goose grass (*Eleusine indica*), Johnson grass (*Sorghum halepense*), crabgrass (*Digitaria violascence*), dent foxtail (*Alopecurus aegualis*), Causeway grass (*Poa annua*), western wheatgrass (*Agropvron kamoji*), fall panicum (*Panicum dichotomiflorum*), *Paspalum thunbergii,* wild oats (*Avena fatua*); cyperaceous weeds such as purple nutsedge (*Cyperus rotundus*); and broad-leaved weeds such as green amaranth (*Amaranthus retroflexus*), lamb's quaters (*Chenopodium album*), common chickweed (*Stellaria media*), hogweed (*Ambrosia elatior*), Polygonum sp., French weed (*Galinsoga paruviflor*) and *Trickly sida (Sida stinosa).*

The compound of this invention has little or no phytotoxicity against crops and is useful for controlling weeds in the locus where soybean, cotton, corn, wheat, sunflower, sugar beet, etc. are cultivated or will be cultivated. In particular, when applied to the locus where soybean, sugar beet and cotton are cultivated or will be cultivated, the compound of this invention exhibits a marked selective herbicidal effect which cannot be observed with conventional herbicides.

The compound of formula (I) provided by this invention can be applied to upland arms, aquatic paddies, orchards, lawns, forest seedling fields, and nonagricultural lands, particularly to the upland farms in which such crops as cited above are cultivated or will be cultivated.

The compound of this invention may be directly sprayed to the locus requiring herbicidal control. But good results can be obtained by mixing it with ordinary herbicidally acceptable carriers or diluents, optionally together with adjuvants, and processed in a customary manner into usual forms of agricultural chemicals such as a wettable powder, an emulsifiable concentrate or granules. The herbicidally acceptable diluents or carriers may be conventional solid or liquid diluents and carriers known in the art. The solid diluents or carriers are, for example, talc, bentonite, clay, kaolin, diatomaceous earth and white carbon. Examples of the liquid diluents or carriers include water, alcohol, dioxane, acetone, cyclohexane, cyclohexanone, dimethylformamide, benzene, xylene and toluene. Suitable adjuvants include, for example surface-active agents such as alkylsulfuric esters, alkylsulfuric acid salts, polyoxyethylene glycol ethers, polyoxyethylene alkylaryl ethers and polyoxyethyelne sorbitan monoalkylates, carboxy methyl cellulose, sodium alginate, polyvinyl alcohol and gum arabic.

The content of the compound of this invention as an active ingredient in the resulting herbicidal composition in various forms may vary depending upon its form, and is, for example, 0.1 to 99% by weight, preferably 1 to 80% by weight. For example, it is 5 to 80% by weight for a wettable powder, 10 to 60% by weight for an emulsifiable concentrate, and 1 to 15% by weight for granules.

The dosage of the compound of this invention may be varied depending upon the locus and method of application, the kind and growth stage of a weed to be controlled, the time of application, etc. Generally, it is, for example, 0.01 to 10 kg, preferably 0.1 to 4 kg, per hectare.

The compound of this invention may be used in admixture with other active compounds such as a fungicide, an insecticide, a miticide, another herbicide and a plant growth regulator to save labor in agricultural chemical application. In particular, the use of the compound of this invention in admixture with another herbicide serves to reduce the amount of the compound of this invention to be used and also save labor. In addition, the synergistic action of the two chemicals is expected to broaden the herbicidal spectrum of the compound of this invention and bring about a greater herbicidal efficacy.

The following examples illustrate the present invention more specifically.

EXAMPLE 1

In a 500 ml eggplant-shaped flask equipped with a stirrer, 17.4 g (75.1 mmoles) of 2-chloro-N-(4,6-dimethoxy-5-pyrimidinyl)acetamide was dissolved in 300 ml of dichloromethane, and 5.22 g of benzyl tributyl ammonium chloride was added. Under ice cooling, 41.5 ml of a 50% aqueous solution of sodium hydroxide was added to the mixture with stirring. Thereafter, a solution of 13.8 g (82.6 mmoles) of N-(1-chloroethyl)-pyrazole hydrochloride in 70 ml of dichloromethane was added dropwise over about 30 minutes. The mixture was stirred further at room temperature for 2 hours. The reaction mixture was washed with water, dried and concentrated. The resulting solid was recrystallized from isopropanol to give 9.26 g of 2-chloro-N-(4,6-dimethoxy-5-pyrimidinyl)-N-(1-(1-pyrazolyl)ethyl)acetamide as a pale yelllow solid which had the following properties.

Melting point: 124.0°–126.5° C.

NMR spectrum ($\delta$, CDCl$_3$): 1.71 (d, 3H), 3.55 (s, 3H), 3.73 (s, 2H), 4.03 (s, 3H), 6.20 (t, 1H), 6.99 (q, 1H), 7.31 (d, 1H), 7.63 (d, 1H), 8.37 (s, 1H).

IR (KBr): 1687 cm$^{-1}$.

EXAMPLE 2

Formulation of a wettable powder:

|  | Parts by weight |
| --- | --- |
| Compound of the invention | 40 |
| Talc | 50 |
| Polyoxyethylene alkylaryl ether-type surface-active agent | 10 |

The above ingredients were uniformly pulverized and mixed to form a wettable powder.

EXAMPLE 3

Formulation of an emulsifiable concentrate:

|  | Parts by weight |
| --- | --- |
| Compound of the invention | 20 |
| Xylene | 55 |
| Dimethylformamide | 15 |
| Polyoxyethylene phenyl ether-type surface-active agent | 10 |

The above ingredients were mixed and dissolved to form an emulsifiable concentrate.

EXAMPLE 4

Formulation of granules:

|  | Parts by weight |
| --- | --- |
| Compound of the invention | 5 |
| Bentonite | 89 |
| Sodium ligninsulfonate | 6 |

The above ingredients were uniformly pulverized and mixed. A small amount of water was added, and the mixture was kneaded with stirring. The kneaded mixture was granulated and dried to form granules.

EXAMPLE 5

Test for herbicidal effect by pre-emergence treatment:

Upland farm soil was filled in square pots (30 cm × 30 cm) (the number of the pots was three for each of the concentrations indicated below). Predetermined amounts of the seeds of weeds indicated in Table 1 were sown and covered with the soil to a sowing depth of about 1 cm.

A water dilution of a wettable powder of each of the compound of this invention and compound 35 of GB No. 2127404A, formulated in accordance with Example 2 above, was uniformly sprayed onto the surface of the soil at the rate of the active ingredient indicated in Table 1. For 30 days after the spraying, the pots were kept in a greenhouse. The herbicidal effect of each of these compounds on the weeds was evaluated on the following scale, and the results are shown in Table 1.

Standards of Evaluation of the Herbicidal Effect (expressed by the proportions of remaining weeds based on a non-treated area)

5: 0 to less than 1%
4: at least 1% to less than 20%
3: at least 20% and less than 40%
2: at least 40% and less than 60%

-continued

1: at least 60% and less than 80%
0: 80% to 100%

TABLE 1

| Test compound | Herbicidal effect | | | | | |
|---|---|---|---|---|---|---|
| | Compound of the invention | | | Compound 35 of GB 2127404A | | |
| | Rate of the active ingredient applied (kg/ha) | | | | | |
| Test plant | 0.25 | 0.5 | 1.0 | 0.25 | 0.5 | 1.0 |
| Barnyard grass | 5 | 5 | 5 | 5 | 5 | 5 |
| Fingergrass | 5 | 5 | 5 | 5 | 5 | 5 |
| Green foxtail | 5 | 5 | 5 | 5 | 5 | 5 |
| Wild oats | 5 | 5 | 5 | 5 | 5 | 5 |
| Johnson grass | 5 | 5 | 5 | 5 | 5 | 5 |
| Fall panicum | 5 | 5 | 5 | 5 | 5 | 5 |
| Buffalo grass | 5 | 5 | 5 | 5 | 5 | 5 |
| Purple nutsedge | 5 | 5 | 5 | 5 | 5 | 5 |
| Green amaranth | 4 | 5 | 5 | 4 | 5 | 5 |
| Lamb's quarters | 4 | 5 | 5 | 4 | 5 | 5 |
| Polygonum longisetum | 4 | 5 | 5 | 4 | 5 | 5 |
| Sicklepod | 2 | 3 | 5 | 2 | 3 | 5 |
| Trickly sida | 5 | 5 | 5 | 5 | 5 | 5 |
| Hent sesbania | 5 | 5 | 5 | 5 | 5 | 5 |

EXAMPLE 6

Test for phytotoxicity to crops by pre-emergence treatment:

In the same way as in Example 5, 10 seeds of each of the crops indicated in Table 2 were sown in pots filled with soil. The crops were grown, and the compound of the invention and compound 35 of GB No. 2127404A were applied, in the same way as in Example 5. The degree of phytotoxicity of each of the applied compounds to the crops was evaluated on the following standards, and the results are shown in Table 2.

Degree of Phytotoxicity

−: no injury
±: slight injury
+: small injury
++: medium injury
+++: heavy injury
X: withered

TABLE 2

| Test compound | Phytotoxicity | | | | | | | |
|---|---|---|---|---|---|---|---|---|
| | Compound of the invention | | | | Compound 35 of GB 2127404A | | | |
| | Rate of the active ingredient applied (kg/ha) | | | | | | | |
| Test crop | 0.25 | 0.5 | 1.0 | 2.0 | 0.25 | 0.5 | 1.0 | 2.0 |
| Soybean | − | − | − | − | − | − | ± | + |
| Sugar beet | − | − | − | − | − | ± | + | ++ |
| Cotton | − | − | − | − | − | ± | ++ | ++ |
| Sunflower | − | − | − | − | − | − | ± | + |
| Rape | − | − | − | − | − | − | − | − |

EXAMPLE 7

Field test:

An upland field was plowed and test areas each having an area of 2 m² (2 m×1 m) in which ridges were spaced from each other by a distance of 15 cm were provided. In each area, two seeds of each crop were sown in each rigde at six sites spaced from each other by a distance of 15 cm, and seeds of weeds in a predetermined amount were sown, on June 10. Thereafter, the surface of the soil was levelled. A wettable powder of each of the compounds indicated in Table 3, formulated as in Example 2, was diluted with water to a predetermined concentration, and sprayed onto the soil surface in an amount of 200 ml per area.

In accordance of the standards of valuation in Examples 5 and 6, the phytotoxicity to crop and the herbicidal effect were examined 45 days after the treatment of the soil surface with the chemical. The results are shown in Table 3.

During the test period, the total rainfall was 350 mm.

TABLE 3

| Test compound | Compound of the invention | | | Compound 35 of GB 2127404A | | |
|---|---|---|---|---|---|---|
| | Rate of the active ingredient applied (kg/ha) | | | | | |
| Test plant | 1.0 | 1.5 | 2.0 | 1.0 | 1.5 | 2.0 |
| Phytotoxicity | | | | | | |
| Soybean | − | − | − | − | − | ± |
| Sugar beet | − | − | − | − | ± | + |
| Cotton | − | − | − | − | ± | + |
| Sunflower | − | − | − | − | − | ± |
| Rape | − | − | − | − | − | − |
| Herbicidal effect | | | | | | |
| Barnyard grass | 5 | 5 | 5 | 5 | 5 | 5 |
| Fingergrass | 5 | 5 | 5 | 5 | 5 | 5 |
| Green foxtail | 5 | 5 | 5 | 5 | 5 | 5 |
| Wild oats | 5 | 5 | 5 | 5 | 5 | 5 |
| Johnson grass | 5 | 5 | 5 | 5 | 5 | 5 |
| Fall panicum | 5 | 5 | 5 | 5 | 5 | 5 |
| Purple nutsedge | 4 | 5 | 5 | 4 | 5 | 5 |
| Green amaranth | 5 | 5 | 5 | 5 | 5 | 5 |
| Lamb's quarters | 5 | 5 | 5 | 5 | 5 | 5 |
| Polygonum longisetum | 5 | 5 | 5 | 5 | 5 | 5 |
| Tricly sida | 5 | 5 | 5 | 5 | 5 | 5 |
| Hent sesbania | 5 | 5 | 5 | 5 | 5 | 5 |
| Sicklepod | 4 | 5 | 5 | 4 | 5 | 5 |

EXAMPLE 8

Field test:

An upland field was plowed and test areas each having an area of 14 m² (7 m×2 m) in which ridges were spaced from each other by a distance of 40 cm were provided. In each area, two seeds of each crop were sown in each rigde at nine sites spaced from each other by a distance of 20 cm, and seeds of weeds in a predetermined amount were sown, on April 26. Thereafter, the surface of the soil was levelled. A wettable powder of each of the compounds indicated in Table 3, formulated as in Example 2, was diluted with water to a predetermined concentration, and sprayed onto the soil surface in an amount of 1400 ml per area.

In accordance of the standards of valuation in Examples 5 and 6, the phytotoxicity to crop and the herbicidal effect were examined 45 days after the treatment of the soil surface with the chemical. The results are shown in Table 4.

During the test period, the total rainfall was 30 mm.

While Example 7 was performed under natural conditions in the rainy season in Japan (very humid and rainy season), Example 8 was performed under natural conditions in the dry spring season in Japan.

TABLE 4

| Test compound | Compound of the invention | | | Compound 35 of GB 2127404A | | | Metolachlor | | |
|---|---|---|---|---|---|---|---|---|---|
| | Rate of the active ingredient applied (kg/ha) | | | | | | | | |
| Test plant | 1 | 1.5 | 2 | 1 | 1.5 | 2 | 1 | 1.5 | 2 |
| Phytotoxicity | | | | | | | | | |
| Soybean | − | − | − | − | − | ± | − | − | − |
| Sugar beet | − | − | − | − | ± | + | − | ± | + |
| Cotton | − | − | − | − | ± | + | − | − | ± |
| Sunflower | − | − | − | − | − | − | − | ± | + |
| Potato | − | − | − | − | − | − | − | − | − |
| Rape | − | − | − | − | − | − | − | − | ± |
| Herbicidal effect | | | | | | | | | |
| Barnyard grass | 3 | 5 | 5 | 3 | 4 | 5 | 3 | 5 | 5 |
| Fingergrass | 3 | 5 | 5 | 3 | 4 | 5 | 4 | 5 | 5 |
| Green foxtail | 3 | 4 | 5 | 2 | 3 | 5 | 3 | 5 | 5 |
| Wild oats | 1 | 2 | 2 | 1 | 2 | 2 | 2 | 3 | 3 |
| Annual bluegrass | 0 | 4 | 5 | 0 | 4 | 5 | 0 | 3 | 5 |
| Green amaranth | 1 | 2 | 2 | 1 | 2 | 2 | 1 | 2 | 4 |
| Lamb's quarters | 1 | 2 | 2 | 1 | 2 | 2 | 1 | 2 | 3 |
| Polygonum longisetum | 1 | 1 | 2 | 1 | 1 | 2 | 1 | 2 | 2 |

EXAMPLE 9

In the same way as in Examples 5 and 6, each of the active components shown in Table 5 were tested, and their herbicidal effects and crop phytotoxicities were evaluated. The results are shown in Table 5.

TABLE 5

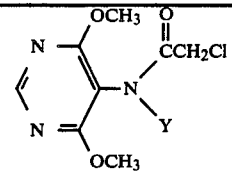

| Y in the compound of the above formula | Rate of the active ingredient applied (kg/ha) | Herbicidal effect | | | | | | Phytotoxicity to crop | | |
|---|---|---|---|---|---|---|---|---|---|---|
| | | A | B | C | D | E | F | G | H | I |
| —CH₂—N (pyrazolyl) (Compound 35 of GB 2127404A) | 1.0 | 5 | 5 | 5 | 5 | 5 | 5 | ± | ++ | + |
| | 0.5 | 5 | 5 | 5 | 5 | 5 | 5 | − | ± | ± |
| | 0.25 | 5 | 5 | 5 | 5 | 5 | 5 | − | − | − |
| —CH—N \| CH₃ (pyrazolyl) (Compound of the invention) | 1.0 | 5 | 5 | 5 | 5 | 5 | 5 | − | − | − |
| | 0.5 | 5 | 5 | 5 | 5 | 5 | 5 | − | − | − |
| | 0.25 | 5 | 5 | 5 | 5 | 4 | 4 | − | − | − |
| —CH—N \| C₂H₅ (pyrazolyl) (Compound of the general formula in GB 2127404A) | 1.0 | 4 | 4 | 3 | 0 | 0 | 0 | − | − | − |
| | 0.5 | 3 | 4 | 3 | 0 | 0 | 0 | − | − | − |
| | 0.25 | 1 | 1 | 2 | 0 | 0 | 0 | − | − | − |
| —CH—N \| CH(CH₃)₂ (pyrazolyl) (Compound of the | 1.0 | 0 | 0 | 0 | 0 | 0 | 0 | − | − | − |
| | 0.5 | 0 | 0 | 0 | 0 | 0 | 0 | − | − | − |
| | 0.25 | 0 | 0 | 0 | 0 | 0 | 0 | − | − | − |

TABLE 5-continued

| Y in the compound of the above formula | Rate of the active ingredient applied (kg/ha) | Herbicidal effect | | | | | | Phytotoxicity to crop | | |
|---|---|---|---|---|---|---|---|---|---|---|
| | | A | B | C | D | E | F | G | H | I |
| general formula in GB 2127404A) | | | | | | | | | | |

In Table 5, the plants are symbolically designated as follows:
 A: barnyard grass
 B: fingergrass
 C: green foxtail
 D: wild oats
 E: Green amaranth
 F: Polygonum longisetum
 G: soybean
 H: cotton
 I: sugar beet

What is claimed is:

1. 2-Chloro-N-(4,6-dimethoxy-5-pyrimidinyl)-N-[1-(1-pyrazolyl)ethyl]acetamide of the following formula:

(I)

2. A herbicidal composition comprising a herbicidally effective amount of 2-chloro-N-(4,6-dimethoxy-5-pyrimidinyl)-N-[1-(1-pyrazolyl)ethyl]acetamide of the following formula (I)

as an active ingredient and a herbicidally acceptable diluent or carrier.

3. The composition of claim 2 wherein the amount of the compound of formula (I) is 0.1 to 99% by weight.

4. A method of controlling weeds which comprises applying a herbicidally effective amount of 2-chloro-N-(4,6-dimethoxy-5-pyrimidinyl)-N-[1-(1-pyrazolyl)ethyl]-acetamide of the following formula (I)

to the locus where the weeds are growing or will grow.

5. The method of claim 4 wherein the amount of the compound of formula (I) applied is 0.01 to 10 kg/ha of the locus.

6. The method of claim 4 wherein the locus is an upland farm where soybean is cultivated or will be cultivated.

7. The method of claim 4 wherein the locus is an upland farm where sugar beet is cultivated or will be cultivated.

8. The method of claim 4 wherein the locus is an upland farm where cotton is cultivated or will be cultivated.

* * * * *